United States Patent
Gidekel et al.

(10) Patent No.: US 8,415,271 B2
(45) Date of Patent: Apr. 9, 2013

(54) BIOFERTILIZER FORMULATION

(75) Inventors: Manuel Gidekel, Santiago (CL); Ana Gutierrez, Santiago (CL); Leticia Barrientos, Temuco (CL); Gustavo Cabrera, Temuco (CL); Graciela Berrios, Temuco (CL); Ivan Mihovilovic, Miami, FL (US)

(73) Assignee: Uxmal S.A., Santiago (CL)

( * ) Notice: Subject to any disclaimer, the term of this patent is extended or adjusted under 35 U.S.C. 154(b) by 0 days.

(21) Appl. No.: 12/451,022

(22) PCT Filed: Apr. 21, 2008

(86) PCT No.: PCT/US2008/005131
§ 371 (c)(1),
(2), (4) Date: Apr. 19, 2010

(87) PCT Pub. No.: WO2008/130701
PCT Pub. Date: Oct. 30, 2008

(65) Prior Publication Data
US 2010/0234222 A1    Sep. 16, 2010

Related U.S. Application Data

(60) Provisional application No. 60/925,444, filed on Apr. 21, 2007.

(51) Int. Cl.
*A01N 59/04* (2006.01)
*A01N 25/00* (2006.01)
*A01G 29/00* (2006.01)

(52) U.S. Cl.
USPC .................. 504/101; 504/116.1; 47/48.5

(58) Field of Classification Search .................. None
See application file for complete search history.

(56) References Cited

U.S. PATENT DOCUMENTS

| | | | |
|---|---|---|---|
| 5,935,839 A * | 8/1999 | Kloepper et al. | 435/252.1 |
| 6,069,301 A | 5/2000 | Carozzi et al. | |
| 2003/0194419 A1 | 10/2003 | Sun et al. | |
| 2005/0060930 A1 | 3/2005 | Kiss et al. | |
| 2005/0262586 A1 * | 11/2005 | Gidekel et al. | 800/279 |
| 2006/0137042 A1 | 6/2006 | Plesch et al. | |

* cited by examiner

*Primary Examiner* — Alton Pryor
(74) *Attorney, Agent, or Firm* — John Dodds

(57) ABSTRACT

Strains of psychrophilic bacteria isolated from the rizosphere of *Deschampsia antarctica* are characterized and biofertilizer compositions comprising one or more of these psychrophilic bacteria strains are disclosed.

23 Claims, 15 Drawing Sheets

Figure 1:
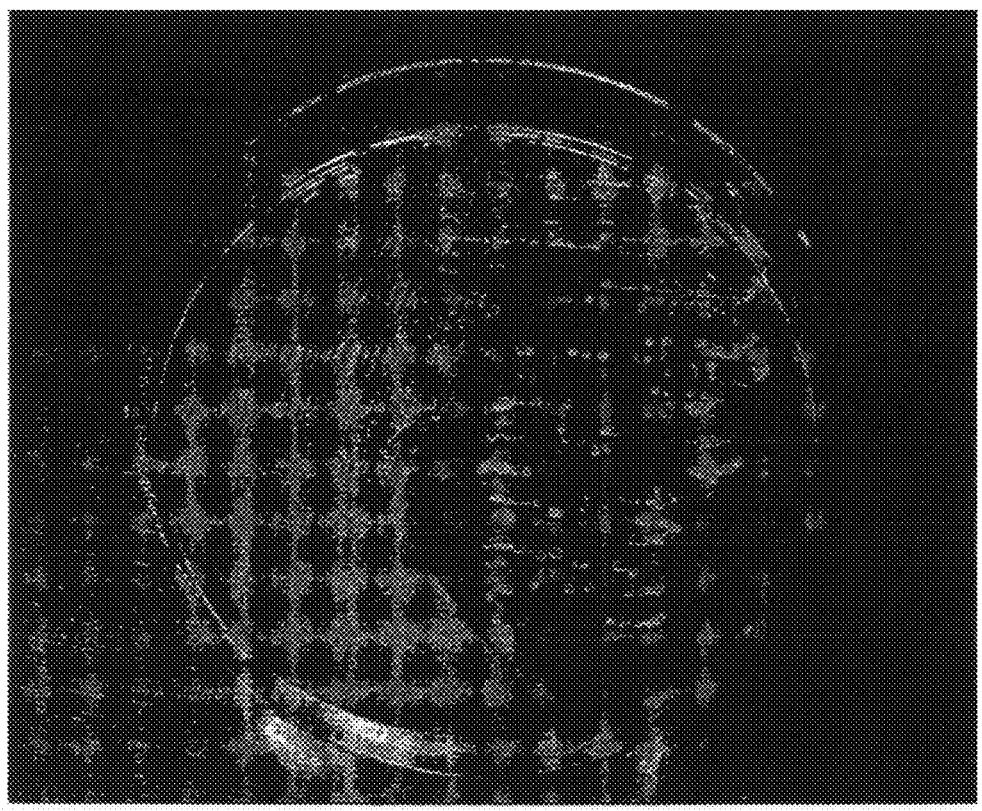

```
Pseudomonas sp. Nj-55 partial 16S rRNA gene, strain Nj-55
Length=1500

Score = 1019 bits (514),  Expect = 0.0
 Identities = 520/522 (99%), Gaps = 0/522 (0%)
 Strand=Plus/Plus Query  1
TATTACCGCGGCTGCTGGCACAGAGTTAGCCGGTGCTTATTCTGTCGGTAACGTCAAAAC   60

||||||||||||||||||||||||||||||||||||||||||||||||||||||||||
Sbjct  979
TATTACCGCGGCTGCTGGCACAGAGTTAGCCGGTGCTTATTCTGTCGGTAACGTCAAAAC   1038

Query  61
AGCAAAGTATTAATTTACTGCCCTTCCTCCCAACTTAAAGTGCTTTACAATCCGAAGACC   120

||||||||||||||||||||||||||||||||||||||||||||||||||||||||||
Sbjct  1039
AGCAAAGTATTAATTTACTGCCCTTCCTCCCAACTTAAAGTGCTTTACAATCCGAAGACC   1098

Query  121
TTCTTCACACACGCGGCATAGCTGGATCAGGCTTTCGCCCATTGTCCAATATTCCCCACT   180
                    ||||||||||||||||||
||||||||||||||||||||||||||||||||||||||||||||
Sbjct  1099
TTCTTCACACACGCGGCATGGCTGGATCAGGCTTTCGCCCATTGTCCAATATTCCCCACT   1158

Query  181
GCTGCCTCCCGTAGGAGTCTGGACCGTGTCTCAGTTCCAGTGTGACCGATCATCCTCTCA   240
             ||||||||||||||||||||||||||||||||||||||||||||||||
||||||||||||
Sbjct  1159
GCTGCCTCCCGTAGGAGTCTGGACCGTGTCTCAGTTCCAGTGTGACTGATCATCCTCTCA   1218

Query  241
GACCAGTTACGGATCGTCGCCTTGGTGAGCCATTACCCCACCAACTAGCTAATCCGACCT   300

||||||||||||||||||||||||||||||||||||||||||||||||||||||||||
Sbjct  1219
GACCAGTTACGGATCGTCGCCTTGGTGAGCCATTACCCCACCAACTAGCTAATCCGACCT   1278

Query  301
AGGCTCATCTGATAGCGCAAGGCCCGAAGGTCCCCTGCTTTCTCCCGTAGGACGTATGCG   360

||||||||||||||||||||||||||||||||||||||||||||||||||||||||||
Sbjct  1279
AGGCTCATCTGATAGCGCAAGGCCCGAAGGTCCCCTGCTTTCTCCCGTAGGACGTATGCG   1338

Query  361
GTATTAGCGTCCGTTTCCGAACGTTATCCCCCACTACCAGGCAGATTCCTAGGCATTACT   420

||||||||||||||||||||||||||||||||||||||||||||||||||||||||||
Sbjct  1339
GTATTAGCGTCCGTTTCCGAACGTTATCCCCCACTACCAGGCAGATTCCTAGGCATTACT   1398
```

Fig. 4.

```
Query  421
       CACCCGTCCGCCGCTCTCAAGAGAAGCAAGCTTCTCTCTACCGCTCGACTTGCATGTGTT  480
       ||||||||||||||||||||||||||||||||||||||||||||||||||||||||||||
Sbjct  1399
       CACCCGTCCGCCGCTCTCAAGAGAAGCAAGCTTCTCTCTACCGCTCGACTTGCATGTGTT  1458

Query  481  AGGCCTGCCGCCAGCGTTCAATCTGAGCCAGGATCAAACTCT  522
            ||||||||||||||||||||||||||||||||||||||||||
Sbjct  1459 AGGCCTGCCGCCAGCGTTCAATCTGAGCCAGGATCAAACTCT  1500
```

Fig. 4 cont.

```
Pseudomonas trivialis strain BIHB 749 16S ribosomal RNA gene,
partial sequence
Length=1495

Score = 1027 bits (518),  Expect = 0.0
 Identities = 521/522 (99%), Gaps = 0/522 (0%)
 Strand=Plus/Plus Query  2
AGAGTTTGATCCTGGCTCAGATTGAACGCTGGCGGCAGGCCTAACACATGCAAGTCGAGC  61

||||||||||||||||||||||||||||||||||||||||||||||||||||||||||||
Sbjct  1
AGAGTTTGATCCTGGCTCAGATTGAACGCTGGCGGCAGGCCTAACACATGCAAGTCGAGC  60

Query  62
GGTAGAGAGAAGCTTGCTTCTCTTGAGAGCGGCGGACGGGTGAGTAATGCCTAGGAATCT  121

||||||||||||||||||||||||||||||||||||||||||||||||||||||||||||
Sbjct  61
GGTAGAGAGAAGCTTGCTTCTCTTGAGAGCGGCGGACGGGTGAGTAATGCCTAGGAATCT  120

Query  122
GCCTGGTAGTGGGGGATAACGTTCGGAAACGGACGCTAATACCGCATACGTCCTACGGGA  181

||||||||||||||||||||||||||||||||||||||||||||||||||||||||||||
Sbjct  121
GCCTGGTAGTGGGGGATAACGTTCGGAAACGGACGCTAATACCGCATACGTCCTACGGGA  180

Query  182
GAAAGCAGGGGACCTTCGGGCCTTGCGCTATCAGATGAGCCTAGGTCGGATTAGCTAGTT  241

||||||||||||||||||||||||||||||||||||||||||||||||||||||||||||
Sbjct  181
GAAAGCAGGGGACCTTCGGGCCTTGCGCTATCAGATGAGCCTAGGTCGGATTAGCTAGTT  240

Query  242
GGTGAGGTAATGGCTCACCAAGGCTACGATCCGTAACTGGTCTGAGAGGATGATCAGTCA  301
                |||||||||||||||||||||||||||
||||||||||||||||||||||||||||||||
Sbjct  241
GGTGAGGTAATGGCTCACCAAGGCGACGATCCGTAACTGGTCTGAGAGGATGATCAGTCA  300

Query  302
CACTGGAACTGAGACACGGTCCAGACTCCTACGGGAGGCAGCAGTGGGGAATATTGGACA  361

||||||||||||||||||||||||||||||||||||||||||||||||||||||||||||
Sbjct  301
CACTGGAACTGAGACACGGTCCAGACTCCTACGGGAGGCAGCAGTGGGGAATATTGGACA  360

Query  362
ATGGGCGAAAGCCTGATCCAGCCATGCCGCGTGTGTGAAGAAGGTCTTCGGATTGTAAAG  421

||||||||||||||||||||||||||||||||||||||||||||||||||||||||||||
Sbjct  361
ATGGGCGAAAGCCTGATCCAGCCATGCCGCGTGTGTGAAGAAGGTCTTCGGATTGTAAAG  420
```

Fig 5

```
Query  422
       CACTTTAAGTTGGGAGGAAGGGCAGTTACCTAATACGTGATTGTTTTGACGTTACCGACA  481
       ||||||||||||||||||||||||||||||||||||||||||||||||||||||||||||
Sbjct  421
       CACTTTAAGTTGGGAGGAAGGGCAGTTACCTAATACGTGATTGTTTTGACGTTACCGACA  480

Query  482  GAATAAGCACCGGCTAACTCTGTGCCAGCAGCCGCGGTAATA  523
            ||||||||||||||||||||||||||||||||||||||||||
Sbjct  481  GAATAAGCACCGGCTAACTCTGTGCCAGCAGCCGCGGTAATA  522
```

Fig 5 cont

Arthrobacter sp. ON14 partial 16S rRNA gene, isolate ON14
Length=1602

Score = 2878 bits (1452),  Expect = 0.0
 Identities = 1491/1502 (99%), Gaps = 4/1502 (0%)
 Strand=Plus/Minus

```
Query  1     TGGTTACCTTGTTACGACTTAGTCCCAATCGCCAGTCCCACCTTCGACAGCTCCCTCCCC  60
             ||||||||||||||||||||||||||||||||||||||||||||||||||||||||||||
Sbjct  1543  TGGTTACCTTGTTACGACTTAGTCCCAATCGCCAGTCCCACCTTCGACAGCTCCCTCCCC  1484

Query  61    ACAAGGGGGTTAGGCCACCGGCTTCGGGTGTTACCAACTTTCGTGACTTGACGGGCGGTG  120
             ||||||||||||||||||||||||||||||||||||||||||||||||||||||||||||
Sbjct  1483  ACAAGGGGGTTAGGCCACCGGCTTCGGGTGTTACCAACTTTCGTGACTTGACGGGCGGTG  1424

Query  121   TGTACAAGGCCCGGGAACGTATTCACCGCAGCGTTGCTGATCTGCGATTACTAGCGACTC  180
             ||||||||||||||||||||||||||||||||||||||||||||||||||||||||||||
Sbjct  1423  TGTACAAGGCCCGGGAACGTATTCACCGCAGCGTTGCTGATCTGCGATTACTAGCGACTC  1364

Query  181   CGACTTCATGGGGTCGAGTTGCAGACCCCAATCCGAACTGAGACCGGCTTTTTGGGATTA  240
             ||||||||||||||||||||||||||||||||||||||||||||||||||||||||||||
Sbjct  1363  CGACTTCATGGGGTCGAGTTGCAGACCCCAATCCGAACTGAGACCGGCTTTTTGGGATTA  1304

Query  241   GCTCCACCTCACAGTATCGCAACCCATTGTACCGGCCATTGTAGCATGCGTGAAGCCCAA  300
             ||||||||||||||||||||||||||||||||||||||||||||||||||||||||||||
Sbjct  1303  GCTCCACCTCACAGTATCGCAACCCATTGTACCGGCCATTGTAGCATGCGTGAAGCCCAA  1244

Query  301   GACATAAGGGGCATGATGATTTGACGTCGTCCTCACCTTCCTCCGAGTCGACCCCGGCAG  360
                         ||||||||||||||||||||||||||||||||||||||||||||||||
                         |||||||||||
Sbjct  1243  GACATAAGGGGCATGATGATTTGACGTCGTCCTCACCTTCCTCCGAGTTGACCCCGGCAG  1184

Query  361   TCTCCTATGAGTCCCCACCATTACGTGCTGGCAACATAGAACGAGGGTTGCGCTCGTTGC  420
             ||||||||||||||||||||||||||||||||||||||||||||||||||||||||||||
Sbjct  1183  TCTCCTATGAGTCCCCACCATTACGTGCTGGCAACATAGAACGAGGGTTGCGCTCGTTGC  1124
```

Fig. 6 (1/4)

Query  421
GGGACTTAACCCAACATCTCACGACACGAGCTGACGACAACCATGCACCACCTGTAAACC  480

||||||||||||||||||||||||||||||||||||||||||||||||||||||||||||
Sbjct  1123
GGGACTTAACCCAACATCTCACGACACGAGCTGACGACAACCATGCACCACCTGTAAACC  1064

Query  481
GACCGCAAGCGGGGCACCTGTTTCCAGGTATTACCGGTTCATGTCAAGCCTTGGTAAGGT  540
            ||||||||||||||||||||||||| ||
||||||||||||||||||||||||||
Sbjct  1063
GACCGCAAGCGGGGCACCTGTTTCCAGGTATTTCCAGTTCATGTCAAGCCTTGGTAAGGT  1004

Query  541
TCTTCGCGTTGCATCGAATTAATCCGCATGCTCCGCCGCTTGTGCGGGCCCCCGTCAATT  600

||||||||||||||||||||||||||||||||||||||||||||||||||||||||||||
Sbjct  1003
TCTTCGCGTTGCATCGAATTAATCCGCATGCTCCGCCGCTTGTGCGGGCCCCCGTCAATT  944

Query  601
CCTTTGAGTTTTAGCCTTGCGGCCGTACTCCCCAGGCGGGGCACTTAATGCGTTAGCTAC  660

||||||||||||||||||||||||||||||||||||||||||||||||||||||||||||
Sbjct  943
CCTTTGAGTTTTAGCCTTGCGGCCGTACTCCCCAGGCGGGGCACTTAATGCGTTAGCTAC  884

Query  661
GGCGCGGAAAACGTGGAATGTCCCCCACACCTAGTGCCCAACGTTTACGGCATGGACTAC  720

||||||||||||||||||||||||||||||||||||||||||||||||||||||||||||
Sbjct  883
GGCGCGGAAAACGTGGAATGTCCCCCACACCTAGTGCCCAACGTTTACGGCATGGACTAC  824

Query  721
CAGGGTATCTAATCCTGTCCGCTCCCCATGCTTTCGCTCCTCAGCGTCAGTTAATGCCCA  780
              |||||||||||||||||
||||||||||||||||||||||||||||||||||||||||
Sbjct  823
CAGGGTATCTAATCCTGTTCGCTCCCCATGCTTTCGCTCCTCAGCGTCAGTTAATGCCCA  764

Query  781
GAGACCTGCCTTCGCCATCGGTGTTCCTCCTGATATCTGCGCATTTCACCGCTACACCAG  840

||||||||||||||||||||||||||||||||||||||||||||||||||||||||||||
Sbjct  763
GAGACCTGCCTTCGCCATCGGTGTTCCTCCTGATATCTGCGCATTTCACCGCTACACCAG  704

Query  841
GAATTCCAGTCTCCCCTACATCACTCTAGTCTGCCCGTACCCACCGCAGATCCGGGGTTG  900
                ||||||||||||||||||||||||||||||||||||||||||||||||||||||||
||||
Sbjct  703
GAATTCCAGTCTCCCCTACATCACTCTAGTCTGCCCGTACCCACCGCAGATCCGGAGTTG  644

Fig. 6 (2/4)

```
Query  901
AGCCCCGGACTTTCACGGCAGACGCGACAAACCGCCTACGAGCTCTTTACGCCCAATAAT  960
       ||||||||||||||||||||||||||||||||||||||||||||||||||||||||||||
Sbjct  643
AGCCCCGGACTTTCACGGCAGACGCGACAAACCGCCTACGAGCTCTTTACGCCCAATAAT  584

Query  961
TCCGGATAACGCTTGCGCCCTACGTATTACCGCGGCTGCTGGCACGTAGTTAGCCGGCGC  1020
       ||||||||||||||||||||||||||||||||||||||||||||||||||||||||||||
Sbjct  583
TCCGGATAACGCTTGCGCCCTACGTATTACCGCGGCTGCTGGCACGTAGTTAGCCGGCGC  524

Query  1021
TTCTTCTGCAAGTACCCTCAACCAACAAAAATGCTGGCCTTGTTCCCTACTGAAAGAGGT  1080
       ||||||||||||||||||||||||||||||||||||||||||||||||||||||||||||
Sbjct  523
TTCTTCTGCAAGTACCCTCAACCAACAAAAATGCTGGCCTTGTTCCCTACTGAAAGAGGT  464

Query  1081
TTACAACCCGAAGGCCGTCATCCCTCACGCGGCGTCGCTGCATCAGGCTTTCGCCCATTG  1140
       ||||||||||||||||||||||||||||||||||||||||||||||||||||||||||||
Sbjct  463
TTACAACCCGAAGGCCGTCATCCCTCACGCGGCGTCGCTGCATCAGGCTTTCGCCCATTG  404

Query  1141
TGCAATATTCCCCACTGCTGCCTCCCGTAGGAGTCTGGGCCGTGTCTCAGTCCCAGTGTG  1200
       ||||||||||||||||||||||||||||||||||||||||||||||||||||||||||||
Sbjct  403
TGCAATATTCCCCACTGCTGCCTCCCGTAGGAGTCTGGGCCGTGTCTCAGTCCCAGTGTG  344

Query  1201
GCCGGTCACCCTCTCAGGCCGGCTACCCGTCGTCGCCTTGGTGAGCCATTACCTCACCAA  1260
       ||||||||||||||||||||||||||||||||||||||||||||||||||||||||||||
Sbjct  343
GCCGGTCACCCTCTCAGGCCGGCTACCCGTCGTCGCCTTGGTGAGCCATTACCTCACCAA  284

Query  1261
CAAGCTGATAGGCCGCGAGTCCATCCAAAACCAATAAATCTTTCAACCAAACCCCATGCG  1320
                   ||||||||||||||||||||||||||||||||||||||||||||||||
       ||||||||||||
Sbjct  283
CAAGCTGATAGGCCGCGAGTCCATCCAAAACCAATAAATCTTTCAACAAAACCCCATGCG  224

Query  1321
AGGTAAAGTCAATATCCAGTATTAGACCCCGTTTCCAAGGCTTATCCCAGAGTTAAGGGC  1380
       ||||||||||||||||||||||||||||||||||||||||||||||||||||||||||||
Sbjct  223
AGGTAAAGTCAATATCCAGTATTAGACCCCGTTTCCAAGGCTTATCCCAGAGTTAAGGGC  164
```

Fig. 6 (3/4)

```
Query  1381
AGGTTACTCACGTGTTACTCACCCGTTCGCCACTAATCCCCGACGCAAGCGCCAGTTCAT  1440
       |||||||||||||||||||||||||||||||||||||||||||  ||||||||
Sbjct  163    AGGTTACTCACGTGTTACTCACCCGTTCGCCACTAATCCCC--CGCAAGCG--
GGTTCAT  108

Query  1441
CGTTCGACTTGCATGTGTTAAGCACGCCGCCAGCGTTCATCCTGAGCCAGGATCAAACTC  1500

||||||||||||||||||||||||||||||||||||||||||||||||||||||||||
Sbjct  107
CGTTCGACTTGCATGTGTTAAGCACGCCGCCAGCGTTCATCCTGAGCCAGGATCAAACTC  48

Query  1501   TA  1502
              ||
Sbjct  47     TA  46
```

Fig. 6 (4/4)

BIOFERTILIZER FORMULATION

PRIORITY

This application claims priority of the U.S. provisional application No. 60/925,444 filed on Apr. 21, 2007.

FIELD OF THE INVENTION

The present invention relates to biofertilizers. More specifically, the present invention relates to biofertilizers containing micro organisms.

DESCRIPTION OF RELATED ART

Phosphorus is one of the principle macronutrients necessary in plant growth and development. It is present in soil at levels of 400 to 1200 mg kg$^{-1}$. Its cycle in the biosphere can be described as sedimentary since there is no exchange with the atmosphere. Microorganisms play a central role in the phosphorus cycle. This cycle takes place through oxidation and a cyclical reduction in phosphorate compounds where the electron transfer reactions occur between the states of oxidation of phosphines (−3) to phosphates (+5). The concentration of soluble phosphorus in soil is normally very low, at levels of 1 ppm or less. Cells accept several forms of phosphorus but most is absorbed in the form of $HPO_4^{2-}$ or $H_2PO_4$.

The principle mechanism for the solubilization of mineral phosphate is action of organic acids synthesized by microorganisms in the soil. This causes the acidification of the microbial cell and its surroundings. In this way, the inorganic phosphate can be released from the mineral phosphate by the substitution of $Ca^{2+}$.

A considerable number of bacterial species, most associated with vegetable rhizosphere, are capable of having some beneficial impact on vegetable growth. Therefore, their use as biofertilizers, as agents controlling other organisms and in the improvement of agriculture, has been the subject of research for several years. Nonetheless, most if not all of this work has concentrated on the search for these organisms in temperate and/or tropical environments and largely in alkaline soils.

Low temperatures are known to affect plant nutrient uptake and often phosphorus deficiency is a result of low temperature stress. Cool soil temperatures during early growing season are a factor causing phosphorus deficiency in crop plants. Phosphorus is an essential element for plant growth and development. Plants need phosphorus for synthesizing ATP, sugars and nucleic acids. Plants suffering from phosphorus deficiency appear to be weak and develop late. Phosphorus deficiency also causes the plants to be prone to various biotic stresses.

Our group has concentrated on research of low temperature tolerant plants, especially of *Deschampsia antarchtica* Desv. (Poacea). Deschampsia is a highly tolerant plant to the harsh freezing conditions and it is one of the two vascular plant species that have naturally colonized Maritime Antarctic Peninsula. The physiology and the genetics of this low temperature tolerant plant have been characterized in U.S. patent applications Nos. 11/120,351 and 11/639,474.

We were interested to understand how this low temperature tolerant plant is able to uptake nutrients for its growth and development in extremely low temperatures. The current disclosure is related to the bacteria isolated from the rizoshpere of *Deschampsia antarctica*. The bacteria of the rizhosphere of *Deschampsia antarctica* are extremophiles, i.e. organism requiring extreme conditions to grow and reproduce. These bacteria are able to grow and reproduce in temperatures around 0° C., whereby they can be defined as psychrophilic bacteria.

SUMMARY OF THE INVENTION

The invention according to his disclosure solves a key problem in the production of plants, which is their acquisition of water and nutrients (mainly phosphorus) when the plants are stressed by low temperatures. The invention comprises formulations that contain one or more microorganisms capable of solubilizing phosphorus at low temperatures, specifically starting from 0° C. These microorganisms make it possible for the phosphorus present in phosphorus rock, normally not usable by plants, to be bioavailable for their nutrition. These bacteria also contribute chemical compounds vital to the plant, such as water and indolacetic acid, which is a plant growth-regulating hormone. Since these bacteria excrete siderophore compounds, they also protect the plants against attack from other phytopathogenic organisms.

SHORT DESCRIPTION OF THE DRAWINGS

FIG. 1. Cultivation of bacterial strain DaBac2H isolated from the rhizoshpere of *Deschampsia antarctica* on a Petri dish.

Figure 2:
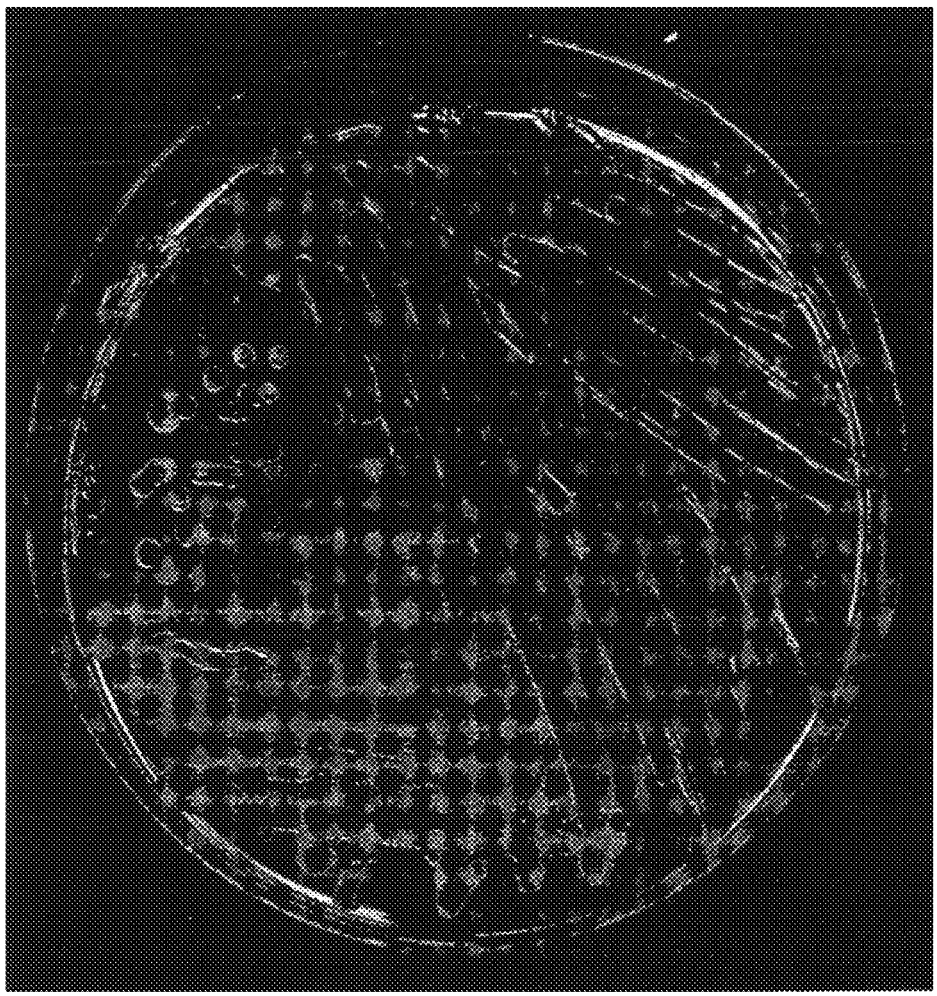

FIG. 2. Cultivation of bacterial strain DaBac MII-9 isolated from the rhizoshpere of *Deschampsia antarctica* on a Petri dish.

Figure 3:
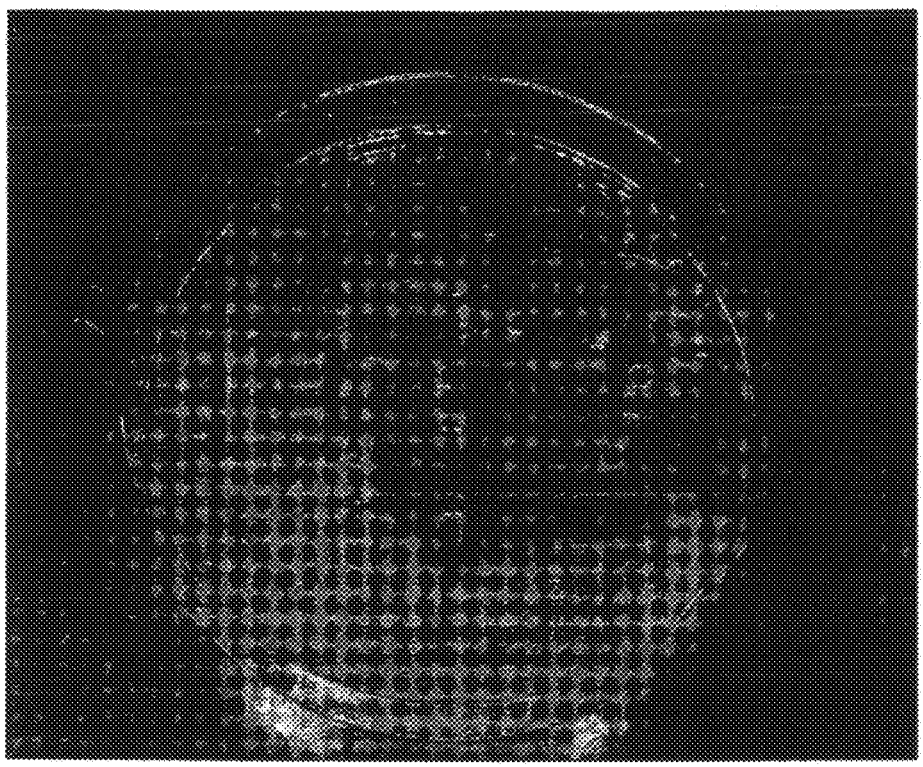

FIG. 3. Cultivation of bacterial strain DaBacTI-8 isolated from the rhizoshpere of *Deschampsia antarctica* on a Petri dish.

FIG. 4. Illustrates the comparison of 16S rRNA gene of DaBac TI-8 strain with *Pseudomonas* sp. Nj-55 partial 16S rRNA gene.

FIG. 5. Illustrates the comparison of 16S rRNA gene of DaBac 2H strain with *Pseudomonas trivialis* strain BIHB 749 partial 16S rRNA gene.

FIG. 6. Illustrates the comparison of 16S rRNA gene of DaBac MII-9 strain with *Arthrobacter* sp ON14 partial 16S rRNA gene.

Figure 7:

FIG. 7. Tomato plants inoculated with A) psychrophilic bacterial biofertilizer, B) commercial biofertilizer. C) Represents a control plant grown without fertilizer. Plants have been grown for 60 days in pots under greenhouse conditions.

Figure 8:
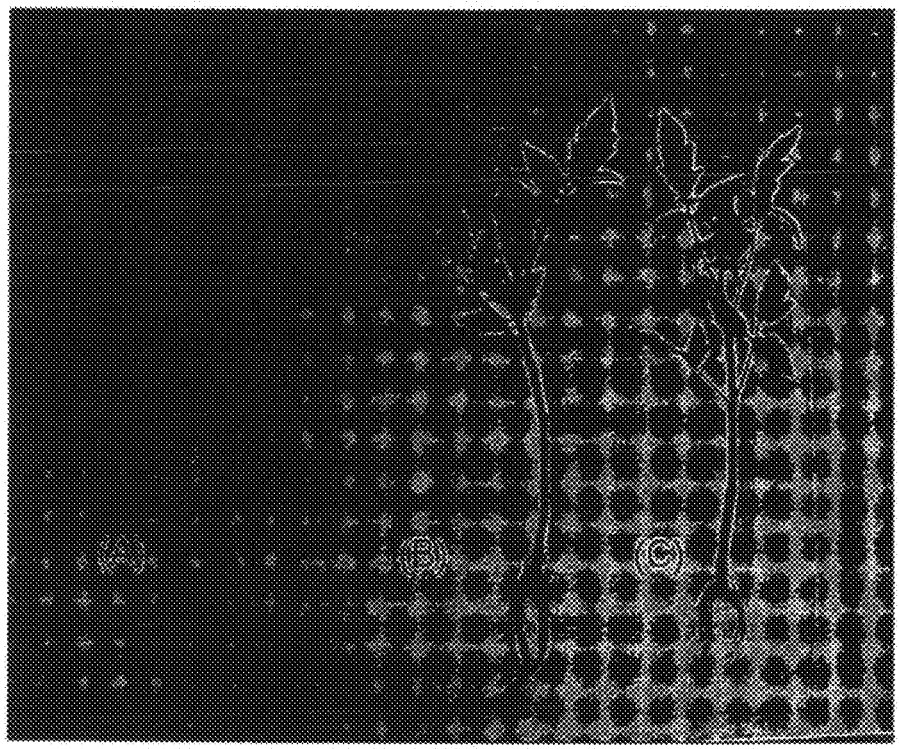

FIG. 8. Illustrates effects of liquid psychrophilic bacterial formulation on development of the roots and shoots tomato plants. Plants were removed from the soil 60 days after planting. (A) Plant grown with liquid psychrophilic bacterial formulation. (B) Plant grown with commercial product. (C) Control plant grown without fertilizer.

Figure 9:
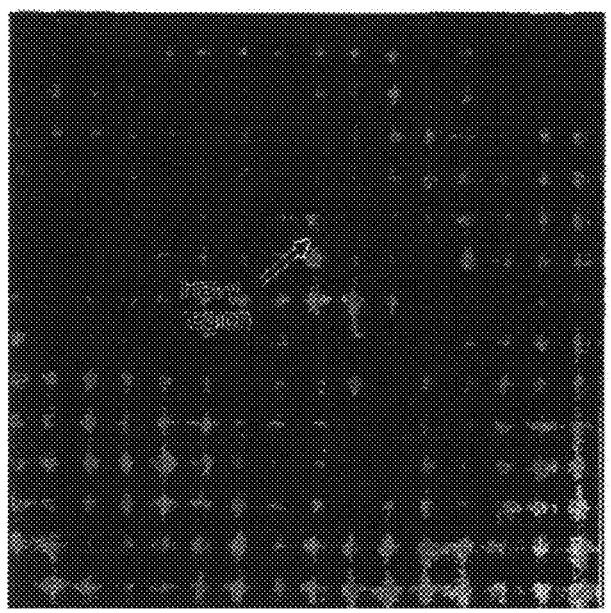

FIG. 9. Germinated tomato seed treated with $10^9$ CFU of psychrophilic bacterial formulation showing a highly developed root region.

Figure 10:
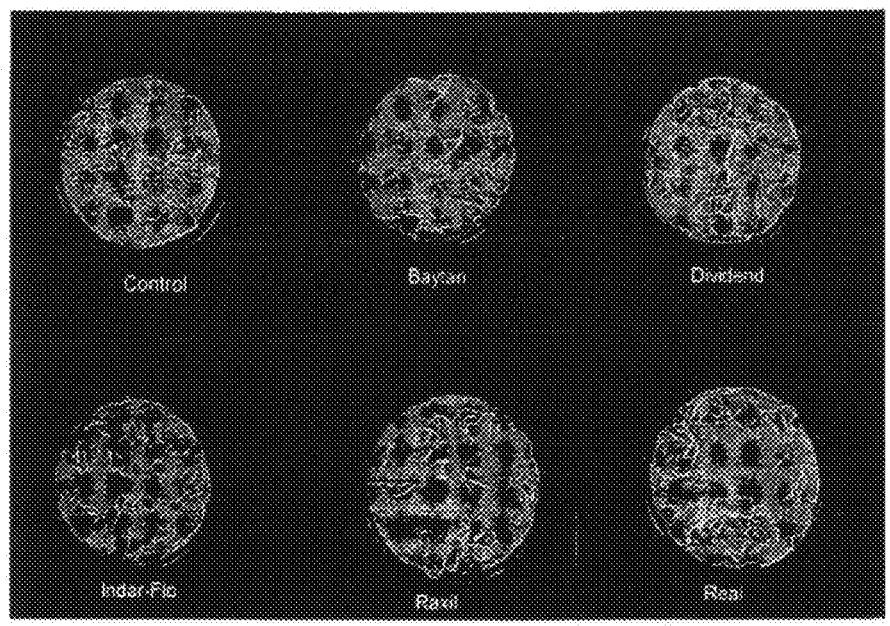

FIG. 10 Germination assay of *Triticum aestivum* var *Kumpa* seeds previously disinfected with commercial fungicides and inoculated with psychrophilic bacterial bioferilizer.

DETAILED DESCRIPTION OF THE INVENTION

A collection of 70 bacterial strains from rizospheric soil of *Descampsia antarcica* was created during the years 200-2005. The strains are kept at a temperature of −80° C. An evaluation of the collection showed that 70% bacteria were psychrophilic or had an optimal growing temperature around 15° C. Furthermore, all of them are able to growth at 4° C.

In order to cultivate the strains of the collection the strains were seeded in falcon tubes with a capacity of 15 ml that contained the medium Luria Bertani (LB). The strains were kept in agitation at 250 rpm and were incubated at room temperature for 24 hours. Based on determination of various characteristics of the strains of the collection we selected three of the strains for further studies: *Pseudomonas antarctica* DaBact TI 8, ATCC deposit designation PTA 8990; *Pseudomonas trivialis* DaBact2H, ATCC deposit designation PTA 8988 and *Arthrobacteria* sp. MII, ATCC deposit designation PTA 8989. Colonies of these bacterial strains on Petri dish cultivation are shown in FIGS. 1, 2 and 3. The morphological and physiological characteristics of the three strains are described below.

Characterization of the Three Bacterial Strains:

The morphological and physiological characters of the strains were studied. Table 1 shows the morphological characteristics of the selected three strains isolated from the rhizosphere of *Deschampsia antarctica*.

TABLE 1

Morphological characteristics of three different bacterial strains isolated from the rhizosphere of *D. antartica*.

| Strains | Colony morphology[a] | Texture | Color | Cell morphology[a] | Gram stain | Growth[b] 4° C. | 37° C. |
|---|---|---|---|---|---|---|---|
| *Pseudomonas antarctica* DaBact TI-8 | Circular | Mucoid | White | Short thin rods | − | + | − |
| *Pseudomonas trivialis* DaBact 2H | Circular | Dry | Moist | Short rods | − | + | − |
| *Arthrobacter* spp. DaBact MII-9 | Circular | Light yellow | Yellow | Short rods | + | + | − |

[a]Growth pattern in solid LB agar. Gram stain: neg, negative; pos, positive
[b]All isolates were able to grow at 10 and 25° C.

The strains of the collection were tested regarding their antibiotic resistance. Antibiotics used for the testing were ampicillin, actinomycinD, streptomycin, gentamycin, kanamycin, tetracycline. Table 2 shows the results of antibiotic resistance of *Pseudomonas antarctica* strain DaBact TI-8, *Pseudomonas rivialis* strain DaBact 2H, and *Arthrobacter* ssp. Strain DaBact MII-9.

TABLE 2

Resistance to different antibiotics found for the different bacteria isolated from *D. antartica* rhizospheric soil.

| Strains | Ampicillin (100 µg ml$^{-1}$) | Actinomycin D (10 µg ml$^{-1}$) | Streptomycin (10 µg ml$^{-1}$) | Gentamycin (20 µg ml$^{-1}$) | Kanamycin (50 µg ml$^{-1}$) | Tetracycline (10 µg ml$^{-1}$) |
|---|---|---|---|---|---|---|
| *Pseudomonas antarctica* DaBact TI-8 | + | + | + | + | + | + |
| *Pseudomonas trivialis* DaBact 2H | + | + | + | + | − | − |
| *Arthrobacter* spp. DaBact MII-9 | − | − | − | + | + | − |

To characterize the bacteria strains further, the strains were grown on solid LB medium with different concentrations of heavy metals. Table 3 shows the results obtained with the three bacterial strains.

TABLE 3

Bacterial growth in solid LB medium with different concentrations of heavy metals.

| Heavy Metal | *Pseudomona antarctica* DaBact TI-8 | *Pseudomona trivialis* DaBact 2H | *Arthrobacter* spp. DaBact MII-9 |
|---|---|---|---|
| Cadmium (mM) | — | 1 | 1 |
| Cobalt (mM) | 1 | 10 | 10 |
| Zinc (mM) | 5 | 5 | 5 |
| Mercury (mM) | 0.2 | 0.4 | 0.4 |

The numbers represent the highest concentration on which the bacteria grew well.

In order to determine which strains of the collection have the capability to solubilize phosphate, a modified PVK culture was used (Pikoyskava, 1948). Potassium phosphate ($K_2HPO_4$) at 10% (p/v) was used as a source of inorganic phosphate which precipitates and becomes tricalcic phosphate (insoluble) when it reacts with calcium chloride.

The phosphate solubilizing capacity was evaluated in two other inorganic sources, namely monobasic calcium phosphate ($Ca(HOP_4)_2 \times H_2O$) and phosphorus rock. The original PVK culture was used to do this (Pikoyskava, 1948). Bromophenol blue was used in preparing the medium with phosphorus rock. This is a reagent that improves the visibility of the halo generated by the solubilization.

The seeding was done superficially using an aliquot (5 µl) of each bacterial suspension. The formation of a halo (precipitation) around the colony on the 5th day after incubation at room temperature was set as the standard for phosphate solubilization (Das, 1989; Singal et al., 1991). The strains solubilized phosphate in PVK on the fifth day after incubation, and the real diameter of the halo formed by these bacteria was measured. The total diameter was measured, deducting the diameter of the bacterial colony thereby allowing a comparison of the ability to solubilize phosphate between the strains studied. All these assays were conducted at 4° C. and the results are shown in Table 4.

TABLE 4

Halo diameter and concentration of phosphorus solubilized by *Deschampsia antarctica* bacterial strains grown in PVK medium, at 4° C., containing different substrates of inorganic phosphorous.

| Strain identification | $Ca_3(PO_4)_2$ halo (mm)[a] | $Ca(HPO_4)_2 \ast H_2O$ | Phosphoric rock (Gafsa) |
|---|---|---|---|
| *Pseudomona antarctica* DaBact TI-8 | 3.3 +/- 0.6 | 5.3 +/- 0.6 | 3.3 +/- 0.6 |
| *Pseudomona Trivialis* DaBact 2H | 5.3 +/- 1.2 | 3.0 +/- 0.0 | 3.3 +/- 0.6 |
| *Arthrobacter* spp. DaBact MII-9 | ND | ND | ND |

[a] the value of the halo corresponds to the mean of three repetitions.
[b] ND: not determined The strains that formed a halo in the three sources of phosphate were selected from the Petri dishes in order to quantify the real capacity of the bacteria taken from the rhizopheric soil of the Deschampsia antarctica to solubilize phosphate. Of the three strains characterized in this disclosure, *Arthrobacter* spp. DaBact MII-9 did not form a measureable halo, but it was carried along in the following experiment. Each of the strains was inoculated in 50 ml falcon tubes containing 25 ml of liquid PVK nutritive culture. Prior to inoculation, a 400 mg P/l of inorganic phosphate was added to each of the tubes. Alternatively 3.2 g of phosphorus rock was added to the tubes. All tubes were sterilized at 120° C. for 30 minutes. The pH in the culture was adjusted to 6.5 using NaOH solution. Each tube was inoculated with strains extracted from the dishes. Then the tubes were incubated for 5 days, shaking constantly at 4° C. The samples were then centrifuged at 10,000 rpm for 10 minutes at 4° C. An aliquot of 1 ml was taken from the supernatant and was used to determine the soluble phosphorus content using the sulphomolybdenum-ascorbic acid method (Murphy and Riley Method, 1962). The readings were compared to those obtained for range of known concentrations that varied from 0.1 to 0.8 ppm of phosphorus. Table 5 provides the quantification of phosphorus solubilized by the selected strains and the change of the pH of the medium due to solubilized phosphorus.

TABLE 5

Concentration of phosphorus solubilized by *Deschampsia antarctica* bacterial strains grown at 4° C., containing inorganic phosphorus and pH values of the medium.

| Strain identification | Phosphoric rock (Gafsa) mg P $L^{-1}$ | Final pH* |
|---|---|---|
| *Pseudomonas antarctica* DaBact TI-8 | 34.3 | 4.2 |
| *Pseudomonas Trivialis* DaBact 2H | 25.5 | 4.4 |

TABLE 5-continued

Concentration of phosphorus solubilized by *Deschampsia antarctica* bacterial strains grown at 4° C., containing inorganic phosphorus and pH values of the medium.

| Strain identification | Phosphoric rock (Gafsa) mg P $L^{-1}$ | Final pH* |
|---|---|---|
| *Arthrobacter* spp. DaBact MII-9 | 0 | ND |

*Inital pH of the PVK medium with inorganic P was 6.5.

Microorganisms have several processes by which P can be mobilized in the soil-plant ecosystem. These processes group together in P solubilization reactions in the soil. During the solubilization of phosphate, calcium-, iron- and aluminum-chelates are formed with different organic acids produced by the microbial metabolism. These acids are known to solubilize in soluble forms of phosphate to a usable form, such as orthophosphate, increasing its potential availability for plants. An aliquot of the microorganism culture broth was used to analyze the type of organic acid excreted by the psychrophilic bacteria strains of this disclosure, and analyzed by using HPLC. It was found that P solubilizes basically because of the excretion of oxalic acids (results not shown).

The bacterial strains were further characterized by measuring enzyme activities with semi quantitative API ZYM method. Results are show below in Table 6.

TABLE 6

Enzymatic activity of the isolated bacterial strains determined by using the semi-quantitative method API ZYM.

| Enzyme Assayed | *Pseudomonas antarctica* DaBact TI-8 | *Pseudomons trivialis* DaBact 2H | *Arthrobacter* spp. DaBact MII-9 |
|---|---|---|---|
| Alkaline phosphatase | + | + | + |
| Acid phosphatase | + | + | + |
| Naphthol-AS-BI-phosphohydrolase | + | + | + |
| Esterase (C4) | + | + | + |
| Esterase Lipase (C8) | + | + | + |
| Lipase (C14) | − | − | + |
| Leucine arylamidase | + | + | + |
| Valine arylamidase | + | + | + |
| Cystine arylamidase | − | − | + |
| α-galactosidase | − | − | + |
| β-galactosidase | − | − | + |
| α-glucosidase | − | − | + |
| N-acetyl-β-glucosaminidase | − | − | + |
| α-mannosidase | − | − | + |

+ means that activity was observed, − means no measurable activity.

Genetic Characterization of the Strains:

16S rDNA was selectively amplified from genomic DNA by PCR with oligonucleotide primers designed to anneal to conserved positions in the 3' and 5' regions of the 16S rRNA genes.

Genomic DNA extraction: The amplification of the 16S rRNA genes was performed directly on cells lysed by treatment at 80° C. for 10 min, followed by 3 min at 100° C.

16S rRNA gene amplification: 16S rRNA was selectively amplified from genomic DNA by PCR with oligonucleotide primers designed to anneal to conserved positions in the 3' and 5' regions of the 16S rRNA genes. Universal bacterial primers were used, and for all the isolates tested the forward primer 8f (5'-AGAGTTTGATCCTGGCTCAG-3') (SEQ ID NO: 4) and 1492r (5'-GGTTACCTTGTTACGACTT-3') (SEQ ID NO: 5) enabled the amplification of 1,502 by of the 16S rRNA gene. PCR amplification was performed in a Peltier Thermal Cycler, PTC-200 (M J Research, USA) in 50 µl of reaction containing 2.5 µl reaction buffer 10×; 2.5 µl of MgCl$_2$ 25 mM; 2.5 µl of each deoxiribonucleotide 2.5 mM; 2.5 µl of each first 10 µM, and 1 U of Taq DNA polymerase (recombinant, Fermentas).

The temperature and cycling conditions were as follows: First, preheating at 94° C. for 2 min; then 30 cycles at 94° C. for 1 mM; 55° C. for 1 mM; and 72° C. for 1.5 min; and a final incubation at 72° C. for 10 min. The presence of PCR products and their concentration were checked by electrophoresis of 5 µl products on a 1% agarose gel, stained with ethidium bromide. A molecular weight marker (1 kb DNA ladder, Fermentas) was included. To generate nearly full-length 16S rRNA clones, the PCR product was ligated into the pGEM-Teasy vector (Promega, Madison, Wis., USA) and the ligation reaction was used to transform competent *Escherichia coli* strain DH5a.

Recombinant colonies were selected on Luria-Bertani agar plates containing 20 µg m$^{-1}$ X-gal (5-bromo-4-chloro-3-indolyl-β-D-galactopyranoside), and 0.5 mM IPTG (isopropyl-β-3-D-thiogalactopyranoside), and 100 g ml$^{-1}$ ampicillin. Plates were incubated overnight at 37° C. The presence of inserts was determined by direct PCR on a sample from white (positive) bacterial colonies, using primers flanking the cloning sites on the vector.

Sequencing was conducted with a Dye Terminator Cycle Sequencing kit and an ABI 3730XL DNASequencer (Applied Biosystems) by Macrogen (Korea). 16S rRNA nucleotide sequences were identified by WWW/BLASTN 2.1.1 (http://www.ncbi.nlm.nih.gov/blast) (Altschul et al. 1990, 1997) using DDBREMBL/GenBank nucleotide sequence databases. The 16S rRNA sequences determined in this study were deposited in the GenBank/EMBL sequence databases.

The sequences obtained were compared with other bacterial sequences available in a public GeneBank: http://www.ncbi.nlm.nih.gov/BLAST (Altschul et al. 1990, 1997)).

The obtained results are summarized here:
1. The bacterial strain DaBac TI-8 showed 99% identity with *Pseudomonas* sp. Nj-55 partial 16S rRNA gene, strain Nj-55, having the sequence identified as AM409368. Comparison of the sequences is shown in FIG. 4.
2. The bacterial strain DaBac 2H showed 99% identity with *Pseudomonas trivialis* strain BIHB 749 16S ribosomal RNA gene, partial sequence, having the sequence identified as DQ885949 Comparison of the sequences is shown in FIG. 5.
3. The bacterial strain DaBac MII-9 showed 99% identity with *Arthrobacter* sp. ON14 partial 16S rRNA gene, isolate ON14, having the sequence identified as AJ810894. Comparison of the sequences is shown in FIG. 6

The invention is now descried by means of examples. The examples are not meant to limit the scope of the invention but are provided as illustrative embodiments of the invention. One skilled in the art appreciates that various modifications of the examples presented here can be done without deviating from the spirit of this invention.

EXAMPLE 1

Liquid Formulation of the Psychrophilic Bacteria Fertilizer for Seed Coating

This example provides a liquid formulation of psychrophilic bacteria fertilizer, where the formulation consists of two separate solutions that are combined before used as seed coating.

For the first solution, the bacteria growths at 25° C., in 1 L flask using an adequate medium, were concentrated by centrifugation in order to separate the solid. This solid with a jelly aspect was suspended in a minimum amount of media. A sun protecting product, such as Congo red or green colorant was added to the media at 1% (w/v).

According to one preferable embodiment all three bacterial strains are used for the first solution in similar initial concentrations. In this case the mixture of three bacterial strains was used having an initial concentration of 10$^{12}$ CFU of each one. However, the biofertilizer formulation can be prepared from any one of the three bacteria strains alone, or a mixture of two or three of the strains can be used as well.

For the second solution, a 1% (w/v) solution of a polysaccharide, such as guar gum, gelan gum, pectin, carboxymetil cellulose, agar-agar, xantan gum (or other food hydrocolloid) was prepared to be used as sticker. In addition, chitosan a known fungicide polymer and elicitor of plant defense reaction may be added at 0.5-1% (w/v). Care is to be taken with chitosan degree of acetylation, it should be lower than 85%, because it could act as bactericidal also.

The two solutions are then mixed together to treat plant seeds as a coating. The seed must be dried before planting and should not be sown before be planted at least 2 h from the application moment.

EXAMPLE 2

Solid State Formulation of the Psychrophilic Bacteria

This example provides a liquid formulation of psychrophilic bacteria fertilizer where the bacteria are encapsulated and the fertilizer is in solid form. Alginate beads were prepared as follows:

1 ml of 30% glycerol was added to 1, 1.5 or 2% sodium alginate solution, depending on the alginate properties (M/G ratio) to obtain a final volume of 25 ml. Then, 250 ml of bacterial culture (obtained from one of the three strains or from a combination of two or more strains) was centrifuged, the cell pellet was washed with saline (0.85% NaCl, w/v) and suspended in 25 ml of alginate mixture and mixed thoroughly. This suspension was added drop wise into a pre-cooled sterile 1.5 or 2% (w/v) aqueous solution of CaCl$_2$ under mild agitation to obtain the bacterial-alginate beads. These beads were allowed to harden for 2-4 h at room temperature. Beads were collected by sieving and were washed several times with sterile water and stored at 4° C. In order to preserve the formulation the fresh wet beads were frozen at −80° C. prior to lyophilization at −45° C. for 15 h. The lyophilized dry beads were stored in sterile glass bottles.

Enumeration of Bacterial Cells in the Beads

To estimate the viable counts, the encapsulated bacteria were released from the beads by resuspending 100 mg of beads in phosphate buffered saline (pH 7.0) for 30 min followed by homogenization. The total number of released bacteria was determined by standard plate count method after incubating at 30° C. for 48 h. At one month intervals the cell densities in the beads were enumerated using similar method as to study the cell loss upon storage. The concentration at the beginning of the experiment was 10$^{12}$ CFU. After 5 months the concentration was still 10$^7$ CFU.

EXAMPLE 3

Effect of the Biofertilizer on Seed Germination

One preferred embodiment of the current invention is a formulation comprising two solutions that are prepared separately and combined at the time of application as described in Example 1 above. The combined solution is then used to coat seeds. It is known that several compounds can inhibit seed germination as being phytotoxic. In order to evaluate a possible negative effect of the seed coating by the biofertilizer, we tested the effect of the biofertilizer on seed germination of tomato and wheat. Germination assays (following the ISTA rules) demonstrated that the psychrophilic biofertilizer inoculation did not prevent or inhibit seed germination, but on the contrary promoted germination.

We tested the effect of the formulation on tomato seeds (*Lycopersicon esculentum* var. *Don* Jose) and wheat seeds (*Triticum aestivum* var. *Kumpa*). The seeds were disinfected with a commercial fungicide before coating with the biofertilizer prepared as described in Example 1. After dropping the seeds in the liquid bacterial formulation they were allowed to dry for one hour and then placed on Petri dishes to germinate in a growth chamber at 25° C. Results from these assays are presented in Tables 7 to 9 and FIGS. 9 and 10.

TABLE 7

Germination assay according to ISTA rules in tomato (variety Don José) seeds inoculated with different amounts (CFU) of psychrophilic bacterial biofertilizer (all three strains were used in equal concentrations to produce the end CFU shown in the first column)

| | Day | |
|---|---|---|
| Treatment | 5 | 14 |
| Control ($H_2O$) | 50 | 93 |
| $10^6$ CFU | 82 | 92 |
| $10^9$ CFU | 79 | 98 |
| $10^{12}$ CFU | 73 | 93 |
| Commercial biofertilizer | 37 | 93 |

TABLE 8

Results of the germination assay of *Triticum aestivum* var Kumpa seeds inoculated with two biofertilizers.

| | Day | |
|---|---|---|
| Treatment | 4 | 8 |
| Control | 84 | 88 |
| Psychrophilic bacterial biofertilizer | 81 | 90 |
| Commercial biofertilizer | 60 | 73 |

TABLE 9

Results of the germination assay of *Lycopersicum esculentum* var Don José seeds inoculated with two biofertilizers.

| | Day | |
|---|---|---|
| Treatment | 5 | 14 |
| Control | 48 | 93 |
| Psychrophilic bacterial biofertilizer | 49 | 98 |
| Commercial biofertilizer | 51 | 98 |

As can be seen from Table 7, the tomato seeds coated with psychrophilic biofertilizer according to this disclosure germinated clearly faster than seeds treated with water or with a commercial biofertilizer. Similarly, results of Table 8 show that wheat seeds germinated faster when coated with the psychrophilic biofertilizer according to this disclosure as compared to seeds treated with water or commercial biofertilizer. Moreover, the wheat seeds possessed a higher germination percentage when coated with the biofertilizer of this disclosure.

The increase in germination and root development could be due to the production and excretion of indole acetic acid IAA) by the bacteria strains here employed. Table 10 shows amounts of IAA in bacterial liquid culture. Clearly, the strain MII9 excreted the highest amounts of IAA

TABLE 10

Determination of the IAA concentration in bacterial liquid culture according to Send and Leopold (1954)

| STRAIN | IAA* (ug $mL^{-1}$) |
|---|---|
| TI8 | 0.62 ± 0.028 |
| MII9 | 5.88 ± 0.238 |
| 2H | 0.98 ± 0.026 |

EXAMPLE 4

Compatibility of the Psychrophilic Biofertilizer with Commercial Fungicides

Because we used a commercial fungicide before coating the seeds in Example 3, we also wanted to make a compatibility assay of the commercial fungicides. In this assay the seeds were disinfected with various commercial fungicides before coating with the psychrophilic bacterial biofertilizer. The results show that the biofertilizer is compatible with at least the following fungicide products: Dividend (Syngenta), Real (BASF) and Raxil (Bayer). Table 11 shows that pre-treatment with a commercial fungicide did not lead to lowering of the concentration of the biofertilizer (CFU/seed) on the seeds. Results in Table 12 show high germination rates in seeds pre-treated with a fungicide before treatment of the psychrophilic bacterial biofertilizer.

TABLE 11

Bacterial count in *Triticum aestivum* var Kumpa seeds previously disinfected and inoculated with psychrophilic bacterial biofertilizer.

| Treatments | CFU/seed |
|---|---|
| Dividend (Syngenta) | $5.4 \times 10^5$ |
| Indar-Flo (Anasac, Dow) | $5.3 \times 10^5$ |
| Baytan (Bayer) | $5.3 \times 10^5$ |
| Real (BASF) | $1.9 \times 10^4$ |
| Raxil (Bayer) | $3.4 \times 10^5$ |
| Control (inoculated without fungicide) | $5.4 \times 10^6$ |

TABLE 12

Results of the germination assay at the 8th day of *Triticum aestivum* var Kumpa seeds previously disinfected with commercial fungicides and inoculated with antarctic biofertilizer.

| Treatments | Germination (%) |
|---|---|
| Dividend (Syngenta) | 94 |
| Indar-Flo (Anasac, Dow) | 83 |
| Baytan (Bayer) | 79 |
| Real (BASF) | 92 |
| Raxil (Bayer) | 95 |
| Control (inoculated without fungicide) | 90 |

EXAMPLE 5

Effect of the Psychrophilic Biofertilizer on Plant Growth and Development

The psychrophilic biofertilizer according to this disclosure also helps in the growth and development of plants. This is due to the fact that these bacteria excrete siderophors (iron chelating compounds). The presence of these compounds was determined qualitatively in isolated strains (results not shown). It is known that siderophors are responsible for protecting the plants against some pathogens. Furthermore, these bacteria also excrete indolacetic acid (Table 10), which is a growth-regulating hormone.

We tested the effect of the biofertilizer on growth and development of tomato plants. The ISTA rules for seed germination were used to evaluate the effectiveness of the bacterial formulation on the tomato growth under controlled conditions. The seeds were coated with the psychrophilic biofertilizer as described in Example 3 above. The tomato plantlets were grown for 30 days and then transplanted to a plastic bags (1 L capacity), filled with sterilized soil, under greenhouse conditions. FIGS. 7 and 8 show plantlets after 60 days from planting them into soil. The root and shoot growth promoting activity of the biofertilizer can clearly be seen.

We analyzed the tomato plants after 60 days from planting the plants into soil. The results are collected into Table 13. It can be seen that the plant height, fresh weight, as well as shoot and root dry weights are clearly higher than those of plants not treated with any biofertilizers. Even if the height of the plants treated with a commercially available biofertilizer was about the same as of the plants treated with the biofertilizer of this invention, the fresh and dry weights were clearly smaller than those of plants treated with biofertilizer according to this invention. The shoot-to-root ratio of plants treated with the biofertilizer of the current disclosure was lower than that of plants treated with water or with a commercial biofertilizer. This was mainly due to the pronounced development of the roots. The root development can be seen from FIG. 8.

TABLE 13

Analysis of tomato plants inoculated with two biofertilizers after 60 days of pot planting and growth under greenhouse conditions (n = 10).

| Treatment | Plant Height (cm) | Fresh weight (g) | Shoot dry weight (g) | Root dry weight (g) | Shoot/Root |
|---|---|---|---|---|---|
| Psychrophilic bacterial biofertilizer | 21.7 | 17.1 | 1.11 | 0.19 | 5.84 |
| Commercial biofertilizer | 21.5 | 13.9 | 0.88 | 0.12 | 7.3 |
| Control | 19.0 | 12.4 | 0.72 | 0.11 | 6.54 |

To analyze the effects of the biofertilizer even further, we conducted a foliar chemical analysis for each treatment in order to establish which were more efficient in plant nutrient uptake; results are presented in Table 14. As is evident from the results, the biofertilizer according to this disclosure clearly increased the contents of nitrogen, phosphorus, potassium, and calcium in the leaves as compared to control plants not coated. Also the content of iron in the leaves was increased. Furthermore, the treatment with a commercially available biofertilizer appeared to give similar results as the treatment with the biofertilizer of this invention. Markedly, however, the calcium concentration of the leaf material was clearly higher after treatment with the biofertilizer of the current invention as compared to treatment with commercial biofertilizer.

TABLE 14

Results from the foliar chemical analysis of tomato plants growth in greenhouse.

| Sample | Antarctic biofertilizer | Comercial biofertilizer | Control |
|---|---|---|---|
| Dry matter | 93.54 | 94.92 | 92.53 |
|  | 2.52 | 2.67 | 1.82 |
| P (%) | 0.52 | 0.50 | 0.14 |
| K (%) | 4.20 | 4.89 | 3.35 |
| Ca (%) | 2.21 | 1.65 | 1.06 |
| Mg (%) | 1.14 | 1.02 | 1.08 |
| Na (%) | 0.20 | 0.16 | 0.21 |
| S (%) | 0.44 | 0.49 | 0.36 |
| Al (ppm) | 155 | 163 | 147 |
| Zn (ppm) | 68 | 63 | 74 |
| Cu (ppm) | 25 | 24 | 27 |
| Fe (ppm) | 153 | 138 | 123 |
| Mn (ppm) | 75 | 54 | 90 |
| B (ppm) | 39 | 38 | 38 |

It is evident form FIGS. 7 and 8 and tables 13 and 14, that the application of the new biofertilizer of this disclosure improves the fertilization of plants, principally the use of P from the soil, along with improving health and development of the plant. The use of this biofertilizer will be vital to crops that have a high need for phosphorated fertilizer, such as wheat, which also has a stage when plant grows during winter period. Since these bacteria are capable of solubilizing phosphorus at a very low temperature (0° C.), plants will be able to survive the stress caused by temperature through the contribution of nutrients in their most critical stage. Because of the foregoing, the biofertilizers according to this invention improve the yield in crops and save considerably phosphorated fertilizers.

One of the biochemical characteristics of the biofertilizer according to this invention is its production of growth regulating compounds, such as indolacetic acid (IAA). IAA is known to enhance root development of plants by improving the absorption of water and nutrients. The fertilizer according to this invention also produces substances that act as natural antibiotics and thereby help controlling growth of phytopathogens in the roots of the plants.

EXAMPLE 6

Effects of the Psychrophilic Biofertilizer on Field Grown Wheat

Effect of the psychrorphilic biofertilizer was tested on field conditions on wheat cultivation in Victoria City, Temuco, Chile. Wheat seeds were disinfected and coated with the psychrophilic bacterial biofertilizer of the present invention as described in Example 3. Control seeds were disinfected and treated with water.

A field of one hectare was directly sowed with the seeds using a random block experimental design with four repetitions per treatments. Further, total yield after the harvest was measured and the yield per unit area of the crop field was calculated. The results are shown in Table 15. As can be seen from the results, the yield of the plants developed from the biofertilizer coated seeds was higher than of control plants and of the same magnitude as control plants grown with phosphorus fertilization. Markedly, phosphorus fertilization did not improve the yield of the plants developed from biofertilizer treated seeds.

TABLE 15

Harvest parameters of wheat seeds coated with biofertilizer

| Treatments | Yield (ton/ha) | Weight 1000 grains (g) |
| --- | --- | --- |
| Control | 4.8 ± 0.2 | 32 ± 3 |
| 50 Kg $P_2O_5$/ha | 4.8 ± 0.5 | 33 ± 3 |
| 100 Kg $P_2O_5$/ha | 5.1 ± 0.3 | 37 ± 3 |
| 150 Kg $P_2O_5$/ha | 5.0 ± 0.4 | 35 ± 3 |
| Biofertilizer | 5.9 ± 0.2 | 40 ± 2 |
| 50 Kg $P_2O_5$/ha + Biofertilizer | 5.6 ± 0.4 | 38 ± 2 |
| 100 Kg $P_2O_5$/ha + Biofertilizer | 5.6 ± 0.3 | 38 ± 2 |
| 150 Kg $P_2O_5$/ha + Biofertilizer | 5.3 ± 0.2 | 38 ± 3 |

The invention according to this application is not limited to use with any specific crop or any specific geographic area. The invention can be used as a biofertilizer for any plants including but not limited to forest plants, for vegetable plants as well as for crops. Moreover, the biofertilizer according to this invention would be beneficial in any areas where low temperatures occur during the growing season. The fertilizer according to this disclosure can be used as seed coating substance, but it can be used as well by direct application into the soil or any other convenient method.

Soy bean is one of the most widely cultivated crop plants that in many areas suffer from low temperature induced problems with availability of water and phosphorus. Use of the psychrophilic bacterial biofertilizer according to this disclosure in soy bean cultivation has the following advantages:

1. The dose of phosphorated fertilizer in crops is reduced and thus the production cost will fall.
2. Crop yield increases because of a better absorption of nutrients and a better health of plants.
3. The fertilizer can be used in extreme temperatures in order to improve production.
4. The fertilizer can be used in acid soils where phosphorus is immobilized in the soil.

The biofertilizer must be applied by using machines for seed treatment to guarantee the homogeneity of application and the uniformity of the covering of the seeds. All inoculation must be conducted preferably in a place where there is no direct solar radiation. The treated seeds must generally be let to aerate for 30 minutes before being planted if the desire is to plant immediately after the product is applied. The application of the product can cause changes in the surface of the seeds. For that reason, the treated seeds will be displaced more slowly in the batching of the seeders that untreated seeds. This means that the machine must be recalibrated before applying the seed.

References

Altschul, S. F., Gish, W., Miller, W., Myers, E. W. and Lipman, D. J. 1990. Basic local alignment search tool. J. Mol. Biol. 215:403-410.

Altschul, S. F, Madden, T. L., Schaffer, A. A., Zhang, J., Zhang, Z., Miller, W. and Lipman, D. J. 1997. Gapped BLAST and PSI-BLAST: A new generation of protein database search programs. Nucl Acids Res 25:3389-3402 Available at http://www.ncbi.nlm.nih.gov/BLAST/.

Das, A. C., 1989. Utilization of insoluble phosphates by soil fungi. J. Indian Soc. Soil Sci. 58:1208-1211.

Murphy, J. and Riley, J. P. 1962. A modified single solution method for the determination of phosphate in natural waters. Anal. Chim. Acta 27:31-36.

Pikovskaya, R. I. 1948. Mobilization of phosphorus in soil in connection with the vital activity of some microbial species. Microbiologiya 17:362-370

Send, S. P.; Leopold, A. C. 1954. Paper chromatography of plant growth regulators and allied compounds. Physiol. Plant. 7: 98-108.

Singal, R., Gupta, R., Kuhad, R. C. and Saxena, R. K. 1991. Solubilization of inorganic phosphates by a Basidiomycetous fungus Cuathus. Indian J. Microbiol. 31:397-401.

What is claimed is:

1. A biofertilizer composition, comprising psychrophilic bacterial strains isolated from rhizosphere of *Deschampsia antarctica*, wherein the composition contains bacterial strains selected from the group consisting of *Pseudomonas antarctica* DaBact TI-9, *Pseudomonas trivialis* DaBact 2H and *Arthrobacter* ssp. DaBact MII-9.

2. The biofertilizer composition of claim 1, wherein the composition contains *Pseudomonas antarctica* DaBact TI-9, *Pseudomonas trivialis* DaBact 2H and *Arthrobacter* ssp. DaBact MII-9 strains in equal concentrations.

3. The biofertilizer composition of claim 1, wherein the fertilizer is prepared before use by combining a solution of bacterial suspension comprising the bacterial strains and a sun protecting product with a polysaccharide solution.

4. The biofertilizer composition of claim 3, wherein the polysaccharide solution contains 1% w/v of a polysaccharide, and the polysaccharide is selected from the group consisting of guar gum, gelan gum, pectin, carboxymetil cellulose, agar, and xantan gum.

5. The biofertilizer composition of claim 1, wherein the biofertilizer composition is for seed coating.

6. The biofertilizer composition of claim 5, wherein the composition improves seed germination.

7. The biofertilizer composition of claim 5, wherein the composition is compatible with any commercial fungicide.

8. The biofertilizer composition of claim 1, wherein the bacterial strains are encapsulated in allignate beads.

9. The biofertilizer composition of claim 1, wherein the biofertilizer is applicable to crop and forest plants.

10. The biofertilizer composition of claim 9, wherein the crop plants are dicotyledonous plants.

11. The biofertilizer composition of claim 10, wherein the crop plant is tomato or soy bean.

12. The biofertilizer composition of claim 9, wherein the crop plants are monocotyledonous plants.

13. The biofertilizer composition of claim 12, wherein the crop plant is wheat.

14. The biofertilizer composition of claim 9, wherein the composition improves phosphorus solubilization in soil.

15. The biofertilizer composition of claim 1, wherein the bacterial strains excrete indolacetic acid (IAA).

16. A method to improve phosphorus solubilization in soil by applying the biofertilizer composition of claim 1 to the plant.

17. A method to improve seed germination by coating the seed with the biofertilizer composition of claim 1.

18. A method to improve seed germination by disinfecting the seed with commercial fungicide and thereafter coating the seed with the biofertilizer composition of claim 5.

19. A method to improve plant growth in low temperatures by applying the biofertilizer composition of claim 1.

20. A method to improve plant uptake of water and minerals by applying the biofertilizer composition of claim 1 to the plant.

21. A method to improve root growth of the plant by applying a biofertilizer of claim 1 to the plant.

22. A biofertilizer composition being prepared before use by combining a bacterial suspension and a polysaccharide solution, wherein said bacterial suspension consists of *Pseudomonas antarctica* DaBact TI-9, *Pseudomonas trivialis* DaBact 2H and *Arthrobacter* ssp. DaBact MII-9 strains each at concentration of $10^{12}$ CFU and 1% (w/v) of sun protecting product, and said polysaccharide solution being 1% (w/v) solution of guar gum, gelan gum, pectin, xarboxymetil cellulose, agar, agar or xantan gum.

23. A biofertilizer composition for use in low temperatures, said biofertilizer composition comprising bacterial strains *Psuedomonas antarctica* DaBact TI-9, *Pseudomonas trivialis* DaBact 2H and *Arthrobacter* ssp. Dabact MII-9.

\* \* \* \* \*

SEQUENCE LISTING

```
<160> NUMBER OF SEQ ID NOS: 5

<210> SEQ ID NO 1
<211> LENGTH: 522
<212> TYPE: DNA
<213> ORGANISM: Pseudomonas antarctica DaBact TI-9
<220> FEATURE:
<221> NAME/KEY: misc_feature
<222> LOCATION: (1)..(522)
<223> OTHER INFORMATION: 16S ribosomal RNA gene, partial sequence

<400> SEQUENCE: 1
tattaccgcg gctgctggca cagagttagc cggtgcttat tctgtcggta acgtcaaaac      60
agcaaagtat taatttactg cccttcctcc caacttaaag tgctttacaa tccgaagacc     120
ttcttcacac acgcggcatg gctggatcag gctttcgccc attgtccaat attccccact     180
gctgcctccc gtaggagtct ggaccgtgtc tcagttccag tgtgactgat catcctctca     240
gaccagttac ggatcgtcgc cttggtgagc cattacccca ccaactagct aatccgacct     300
aggctcatct gatagcgcaa ggcccgaagg tccctgctt tctcccgtag gacgtatgcg      360
gtattagcgt ccgtttccga acgttatccc ccactaccag gcagattcct aggcattact     420
cacccgtccg ccgctctcaa gagaagcaag cttctctcta ccgctcgact tgcatgtgtt     480
```

```
aggcctgccg ccagcgttca atctgagcca ggatcaaact ct            522
```

```
<210> SEQ ID NO 2
<211> LENGTH: 522
<212> TYPE: DNA
<213> ORGANISM: pseudomonas trivialis DaBact 2H
<220> FEATURE:
<221> NAME/KEY: misc_feature
<222> LOCATION: (1)..(522)
<223> OTHER INFORMATION: 16S ribosomal RNA gene, partical sequence

<400> SEQUENCE: 2
```

```
agagtttgat cctggctcag attgaacgct ggcggcaggc ctaacacatg caagtcgagc    60
ggtagagaga agcttgcttc tcttgagagc ggcggacggg tgagtaatgc ctaggaatct   120
gcctggtagt gggggataac gttcggaaac ggacgctaat accgcatacg tcctacggga   180
gaaagcaggg gaccttcggg ccttgcgcta tcagatgagc ctaggtcgga ttagctagtt   240
ggtgaggtaa tggctcacca aggcgacgat ccgtaactgg tctgagagga tgatcagtca   300
cactggaact gagacacggt ccagactcct acggaggca gcagtgggga atattggaca    360
atgggcgaaa gcctgatcca gccatgccgc gtgtgtgaag aaggtcttcg gattgtaaag   420
cactttaagt tgggaggaag ggcagttacc taatacgtga ttgttttgac gttaccgaca   480
gaataagcac cggctaactc tgtgccagca gccgcggtaa ta                      522
```

```
<210> SEQ ID NO 3
<211> LENGTH: 1498
<212> TYPE: DNA
<213> ORGANISM: Arthrobacter ssp DaBact MII-9
<220> FEATURE:
<221> NAME/KEY: misc_feature
<222> LOCATION: (1)..(1498)
<223> OTHER INFORMATION: 16S ribosomal RNA gene, partical sequence

<400> SEQUENCE: 3
```

```
tggttacctt gttacgactt agtcccaatc gccagtccca ccttcgacag ctccctcccc    60
acaaggggt taggccaccg gcttcgggtg ttaccaactt tcgtgacttg acgggcggtg   120
tgtacaaggc ccgggaacgt attcaccgca gcgttgctga tctgcgatta ctagcgactc   180
cgacttcatg gggtcgagtt gcagacccca atccgaactg agaccggctt tttgggatta   240
gctccacctc acagtatcgc aacccattgt accggccatt gtagcatgcg tgaagcccaa   300
gacataaggg gcatgatgat ttgacgtcgt cctcaccttc ctccgagttg accccggcag   360
tctcctatga gtccccacca ttacgtgctg caacataga acgagggttg cgctcgttgc   420
gggacttaac ccaacatctc acgacacgag ctgacgacaa ccatgcacca cctgtaaacc   480
gaccgcaagc ggggcacctg tttccaggta tttccagttc atgtcaagcc ttggtaaggt   540
tcttcgcgtt gcatcgaatt aatccgcatg ctccgccgct tgtgcgggcc cccgtcaatt   600
cctttgagtt ttagccttgc ggccgtactc cccaggcggg gcacttaatg cgttagctac   660
ggcgcggaaa acgtggaatg tcccccacac ctagtgccca acgtttacgg catggactac   720
cagggtatct aatcctgttc gctccccatg ctttcgctcc tcagcgtcag ttaatgccca   780
gagacctgcc ttcgccatcg gtgttcctcc tgatatctgc gcatttcacc gctacaccag   840
gaattccagt ctcccctaca tcactctagt ctgcccgtac ccaccgcaga tccggagttg   900
agccccggac tttcacggca gacgcgacaa accgcctacg agctctttac gcccaataat   960
tccggataac gcttgcgccc tacgtattac cgcggctgct ggcacgtagt tagccggcgc  1020
ttcttctgca agtaccctca accaacaaaa atgctggcct tgttccctac tgaaagaggt  1080
```

```
ttacaacccg aaggccgtca tccctcacgc ggcgtcgctg catcaggctt tcgcccattg    1140
tgcaatattc cccactgctg cctcccgtag gagtctgggc cgtgtctcag tcccagtgtg    1200
gccggtcacc ctctcaggcc ggctacccgt cgtcgccttg gtgagccatt acctcaccaa    1260
caagctgata ggccgcgagt ccatccaaaa ccaataaatc tttcaacaaa acccatgcg     1320 aggtaaagtc aatatccagt attagacccc gtttccaagg cttatcccag agttaagggc    1380
aggttactca cgtgttactc acccgttcgc cactaatccc ccgcaagcgg gttcatcgtt    1440
cgacttgcat gtgttaagca cgccgccagc gttcatcctg agccaggatc aaactcta     1498

<210> SEQ ID NO 4
<211> LENGTH: 20
<212> TYPE: DNA
<213> ORGANISM: artificial sequence
<220> FEATURE:
<223> OTHER INFORMATION: chemically synthetized
<220> FEATURE:
<221> NAME/KEY: misc_feature
<222> LOCATION: (1)..(20)
<223> OTHER INFORMATION: forward primer

<400> SEQUENCE: 4
agagtttgat cctggctcag                                                  20

<210> SEQ ID NO 5
<211> LENGTH: 19
<212> TYPE: DNA
<213> ORGANISM: artificial sequence
<220> FEATURE:
<223> OTHER INFORMATION: chemically syntethized
<220> FEATURE:
<221> NAME/KEY: misc_feature
<222> LOCATION: (1)..(19)
<223> OTHER INFORMATION: primer

<400> SEQUENCE: 5
ggttaccttg ttacgactt                                                   19
```